(12) United States Patent
Kleen et al.

(10) Patent No.: US 7,480,398 B2
(45) Date of Patent: Jan. 20, 2009

(54) METHOD OF REGISTERING A SEQUENCE OF 2D IMAGE DATA WITH 3D IMAGE DATA

(75) Inventors: Martin Kleen, Furth (DE); Marcus Pfister, Erlangen (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 686 days.

(21) Appl. No.: 11/076,536

(22) Filed: Mar. 8, 2005

(65) Prior Publication Data

US 2005/0196028 A1 Sep. 8, 2005

(30) Foreign Application Priority Data

Mar. 8, 2004 (DE) ................ 10 2004 011 154

(51) Int. Cl.
*G06K 9/00* (2006.01)
*G06K 9/36* (2006.01)
*A61B 5/05* (2006.01)

(52) U.S. Cl. ............... 382/128; 382/131; 382/132; 382/154; 382/285; 600/407

(58) Field of Classification Search ........... 382/128, 382/130, 131, 132, 154, 285, 294; 600/101, 600/407, 424
See application file for complete search history.

(56) References Cited

U.S. PATENT DOCUMENTS 5,771,895 A * 6/1998 Slager ................ 600/462

(Continued)

FOREIGN PATENT DOCUMENTS

WO WO 97/28743 8/1997

(Continued)

OTHER PUBLICATIONS

Prause, et al. "Semiautomated segmentation and 3D reconstruction of coronary trees: biplane angiography and intravascular ultrasound data fusion." Medical Imaging 1996: Physiology and Function from Multidimensional Images, Proceedings of SPIE 2709(1996): 82-92.*

(Continued)

*Primary Examiner*—Samir A Ahmed
*Assistant Examiner*—Michael A Newman

(57) ABSTRACT

The present invention relates to a method for registration of a sequence of 2D image data (5) of a hollow channel (2), in particular of a vessel, recorded with an imaging endoluminal instrument (1) when the relative displacement positions of the instrument (1) in the hollow channel (2) are known, with 3D image data (8) of the hollow channel (2). In the method a three-dimensional path of a central axis (10) of a definable section of the hollow channel (2) is determined from the 3D image data (8), the three-dimensional path of the central axis (10) is converted into a rectilinear path by a first transformation of the 3D image data (8) of the definable section of the hollow channel (2) and transformation parameters required for the first transformation are stored. A combined 3D image data record (11) is generated from the sequence of 2D image data (5) by a parallel side-by-side arrangement on a central straight line in accordance with the known relative displacement positions, and is first registered with the transformed 3D image data (9) by equating the central straight line with the rectilinear path of the central axis (10) and suitable translation for superposition of a shared reference point. The combined 3D image data record (11) or 2D image data (5) contained therein is then registered with the 3D image data (3), taking into account the stored transformation parameters.

9 Claims, 3 Drawing Sheets

U.S. PATENT DOCUMENTS

| | | | |
|---|---|---|---|
| 6,148,095 A * | 11/2000 | Prause et al. | 382/131 |
| 6,248,074 B1 | 6/2001 | Ohno et al. | |
| 6,317,621 B1 | 11/2001 | Graumann et al. | |
| 6,389,104 B1 * | 5/2002 | Bani-Hashemi et al. | 378/98.12 |
| 6,501,848 B1 * | 12/2002 | Carroll et al. | 382/128 |
| 6,928,314 B1 * | 8/2005 | Johnson et al. | 600/407 |
| 7,273,469 B1 * | 9/2007 | Chan et al. | 604/96.01 |
| 2002/0106116 A1 | 8/2002 | Knoplioch et al. | |

FOREIGN PATENT DOCUMENTS

WO    WO 98/32371    7/1998

OTHER PUBLICATIONS

Roelandt, et al. "Three-dimensional reconstruction of intracoronary ultrasound images. Rationale, approaches, problems, and directions." Circulation 90(1994): 1044-1055.*

D. Rotger, M. Rosales, J. Garcia, O. Pujol, J. Mauri, P. Radeva, "Active Vessel: A New Multimedia Workstation for Intravascular Ultrasound and Angiography Fusion", IEEE, Computers in Cardiology 2003, pp. 65-68.

* cited by examiner

METHOD OF REGISTERING A SEQUENCE OF 2D IMAGE DATA WITH 3D IMAGE DATA

CROSS REFERENCE TO RELATED APPLICATIONS

This application claims priority to the German application No. 10 2004 011 154.5, filed Mar. 8, 2004 which is incorporated by reference herein in its entirety.

FIELD OF INVENTION

The present invention relates to a method for registering a sequence of 2D image data of a hollow channel, in particular of a vessel, which was recorded with an imaging endoluminal instrument where relative displacement positions of the instrument in the hollow channel are known, with 3D image data of the hollow channel from 3D imaging processes, such as computer tomography (CT), magnetic resonance tomography (MR), 3D angiography or 3D ultrasound.

BACKGROUND OF INVENTION

Imaging endoluminal instruments can be used to record two-dimensional images of the interior of a hollow channel, in particular of a vessel or of a hollow organ. Use is made here of imaging methods such as intravascular ultrasound (IVUS), optical coherence tomography (OCT) or fluorescent imaging. The image is recorded during the continuous or gradual controlled movement of the instrument in the hollow channel. Thus for example imaging intravascular catheters can provide two-dimensional sectional images from the interior of vessels, e.g. from the vascular system of the heart. FIG. 1 shows by way of example a section through the vascular system 3 of the heart, it being possible to identify the imaging catheter 1 inserted into one of the vessels 2. This catheter 1 is moved forward or backward with a movement control device 4 either mechanically or manually in the vessel 2. The trajectory direction of the catheter 1 is indicated by the arrow. During the continuous, controlled movement of the catheter 1 in the vessel 2 two-dimensional sectional images of the vessel are recorded at regular intervals. FIG. 1 shows, on the right, the 2D sectional images 5 which are obtained during the movement of the catheter 1 at various positions in the vessel 2 and which in each case represent a section transverse to the longitudinal axis of the vessel 2. The arrow running along the 2D sectional images 5 represents the trajectory direction of the catheter 1 while the image is being recorded. In the 2D sectional images the vascular wall 7 as well as the central axis 10 of the vessel within the vessel lumen 6 can be seen, on which axis the catheter 1 is guided. Since the longitudinal displacement of the catheter 1 at the time of each recording of a 2D sectional image 5 and thus also the relative displacement positions for each 2D sectional image are known as a result of the controlled catheter movement, the image data for these images can be compiled to form a three-dimensional image data record by taking into account the relative displacement positions.

Furthermore DE 199 19 907 A1 discloses a method for catheter navigation in three-dimensional vascular tree exposures, in which the spatial position of the catheter is detected and blended into a 3D view of a preoperatively recorded vascular tree. For this, use is made of a catheter with an integrated position sensor, via which the respective current spatial position of the catheter tip is detected. This position sensor is registered with the 3D image data before the intervention takes place, using special markers which are visible in the 3D image and which are approached with the catheter. This type of registration is required for all applications in which the recorded 2D image data is to be combined with 3D image data.

SUMMARY OF INVENTION

Based on this prior art, an object of the present invention is to specify a method for registering 2D image data of a hollow channel, recorded with an imaging endoluminal instrument, with 3D image data, said method dispensing with the use of a position sensor.

The object is achieved by the claims. Advantageous embodiments of the method are the subject of the dependent claims or can be taken from the following description and the exemplary embodiments.

In the present method for registering a sequence of 2D image data of a hollow channel, in particular of a vessel, which is recorded using an imaging endoluminal instrument where relative displacement positions of the instrument in the hollow channel are known, with 3D image data of the hollow channel, a three-dimensional path of a central axis of a definable section of the hollow channel is first determined from the 3D image data. This determination of the three-dimensional path of the central axis can for example be undertaken by segmenting the wall of the hollow channel identifiable in the 3D image data, on the basis of which the central axis is determined geometrically. Other image processing algorithms for determining the path of the axis are of course possible. Next this three-dimensional path of the central axis is converted by an isometric first transformation of the 3D image data of the definable section of the hollow channel into a rectilinear path and the transformation parameters required for this transformation are stored for a subsequent reverse transformation. A combined 3D image data record is generated from the sequence of 2D image data by means of a parallel, congruent side-by-side arrangement on a central straight line in accordance with the known relative displacement positions, as is also already known from the prior art. The combined 3D image data record is finally registered by equating the central straight line with the straight path of the central axis of the transformed 3D image data record and by suitable translation for superposition of a shared reference point with this transformed 3D image data. Any differences in resolution between the combined 3D image data record and the transformed 3D image data can be eliminated by a voxel interpolation in all 3 dimensions. A branch of the hollow channel or another prominent or known point can for example be used as a reference point. In this way registration can be achieved by simple translation of the two 3D image data records to one another. After this registration the combined 3D image data record or the 2D image data contained therein is transformed back into the position of the original 3D image data, taking into account the stored transformation parameters. This is achieved preferably by a direct second transformation of the combined 3D image data record or of the 2D image data contained therein, which represents a reverse transformation to the first transformation with the help of the stored transformation parameters. If the original 3D data record was not saved at the time of the first transformation, this is likewise obtained again by a reverse transformation of the transformed 3D image data. As a result of the present method the 2D image data of the section under investigation of the hollow channel now exists registered with the 3D image data record. In addition this 2D image data can be arranged or reconstructed in accordance with the true 3D anatomy of the hollow channel. This reconstruction occurs automatically at the time of the reverse transformation of the combined 3D image data record.

Thus a method is provided for registration of a sequence of 2D image data recorded continuously while the instrument is being guided through a hollow channel with an anatomical 3D image data record, which dispenses with the use of a position sensor. The registration step is greatly simplified by the proposed transformation of the 3D image data, since all that is required is a translation of the two 3D image data records to one another. The present method is suitable here in particular for use with imaging methods such as IVUS, OCT or fluorescent imaging with the help of a catheter or endoscope for registering the image data of vessels or hollow organs with image data from 3D imaging procedures such as CT, MR, 3D angiography or 3D ultrasound. The simple registration means the image data can then be displayed combined in any way for the user, e.g. superposed. The present method can of course also be applied to image data from examinations of other tubular parts of the body, such as intestinal examinations or bronchioscopies.

BRIEF DESCRIPTION OF THE DRAWINGS

The present method is explained again in greater detail below on the basis of an exemplary embodiment in conjunction with the drawings. These show.

DETAILED DESCRIPTION OF INVENTION

Figure 1:
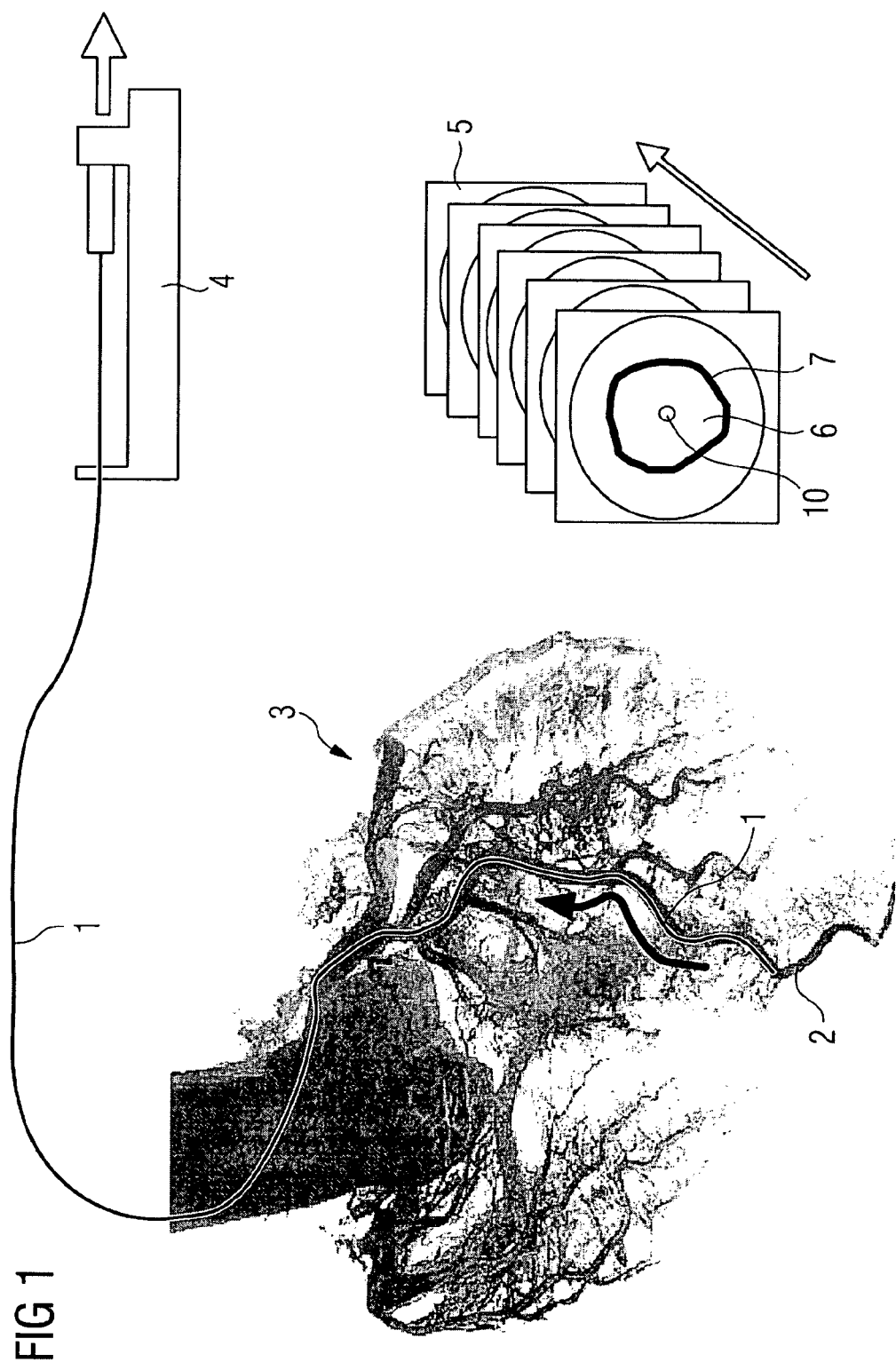
FIG. 1 a representation of the conditions when recording 2D sectional images with a catheter.

In the present example the registration of 2D image data with 3D image data of a vascular section is illustrated by way of example. The recording of a series of 2D image data with a catheter has already been briefly explained in the introductory part of the description on the basis of FIG. 1. The result of this image recording is a sequence of unconnected 2D images 5 with known translation of the longitudinal axis of the vessel appropriate to each image.

Figure 5:
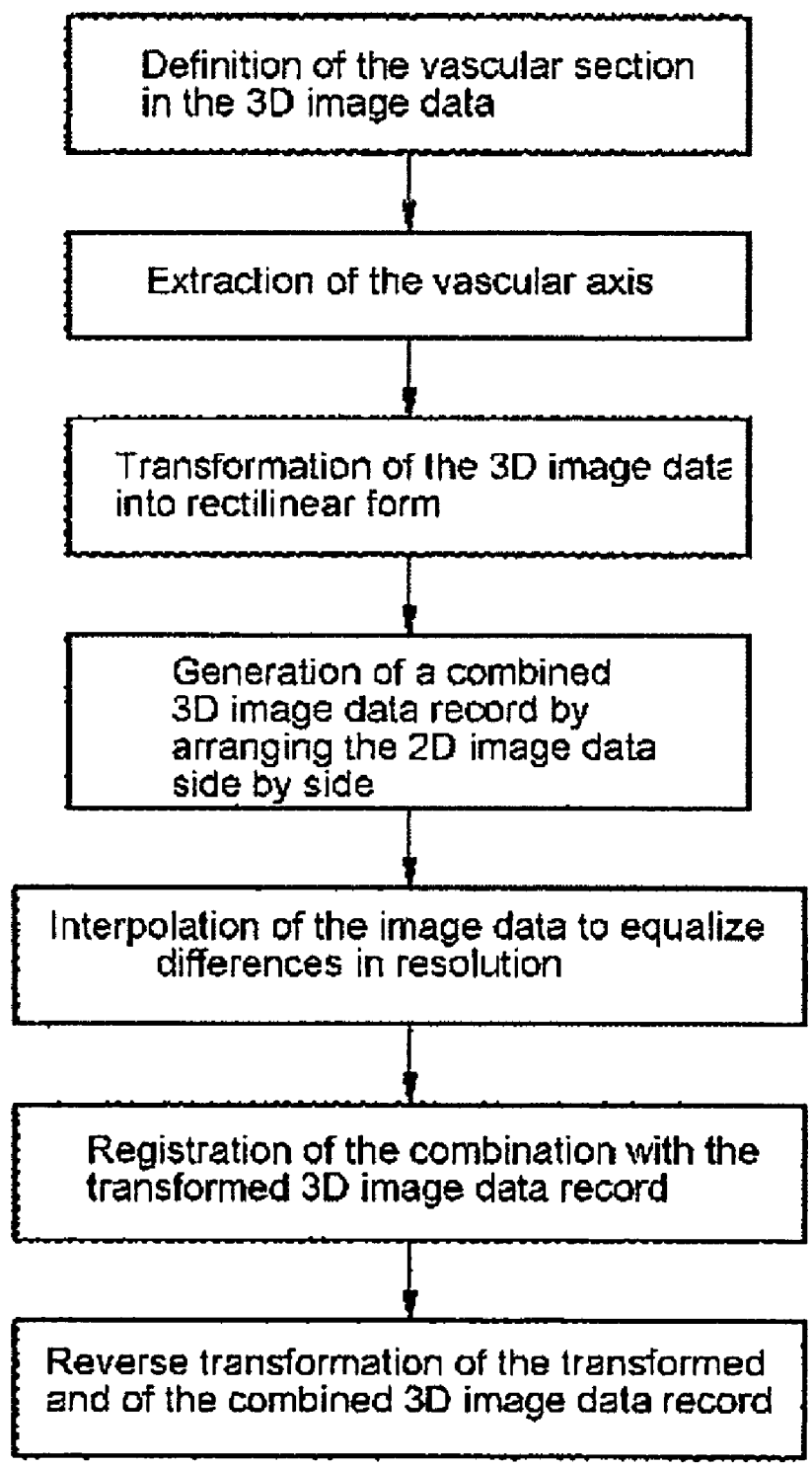

FIG. 5 gives an overview of the individual method steps of the present method.

First a section of the vessel 2 to be merged is defined in the 3D image data displayed to a user by identification of a three-dimensional start point and of a three-dimensional end point. Once the vascular section is specified, the three-dimensional path of the central axis 10 of the vascular section is extracted in this anatomical 3D image data 8. The vascular section is here first segmented, in order to use the segmented data to geometrically determine the path of the central axis 10.

Figure 2:
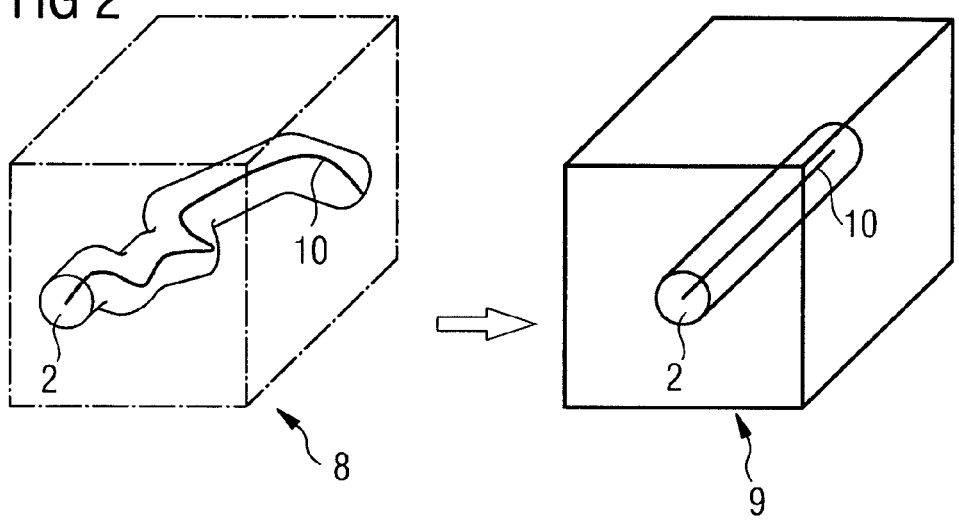
FIG. 2 an example of the transformation of 3D image data of a vascular section into a rectilinear form.

On the basis of this three-dimensional path 10 of the central axis the 3D vascular structure of this vascular section is transformed into a rectilinear or tubular form. This is illustrated in FIG. 2. The parameters of the transformation are stored for the subsequent reverse transformation.

Figure 3:
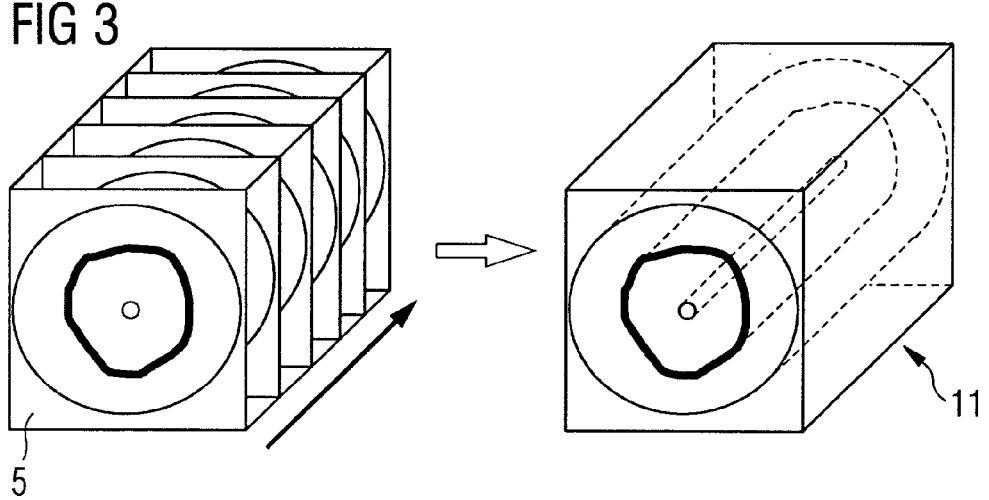
FIG. 3 an example of the generation of the combined 3D image data record from the recorded 2D image data.

As illustrated in FIG. 3, a rectilinear, tubular 3D image data record 11 is generated, likewise by a simple side-by-side arrangement, from the sequence of 2D image data 5 recorded with this instrument. The spacing of the individual 2D images 5 in this 3D data record 11 is specified by the known relative displacement position of the catheter during image recording. The 2D image data 5 is here generally recorded with chronologically constant catheter movement. This is possible thanks to known motor pull-back devices. Any resolution differences between the 3D image data record 11 obtained from the 2D image data 5 and the 3D image data record 8 from the 3D procedure can be eliminated by voxel interpolation in all 3 dimensions.

The last method steps result in two 3D image data records 9, 11, each of which show the vascular section of interest in a rectilinear orientation. These two data records 9, 11 can now be assigned, i.e. registered, by a simple superposition of the central axis and reciprocal translation on the basis of a shared known point. A vascular branch can for example be recorded in the two 3D images by the user as a shared known point and brought into agreement.

Figure 4:
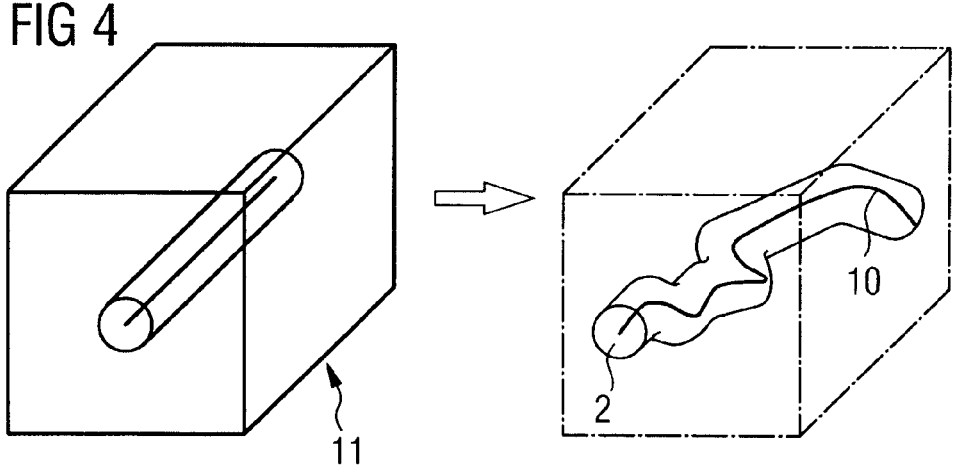
FIG. 4 an illustration of the reverse transformation of the combined 3D image data record and FIG. 5 an overview of the sequence of the method when performing the present method.

After this registration of the two rectilinear-oriented 3D image data records 9, 11 a reverse transformation takes place into the original 3D form. This is illustrated in FIG. 4 on the basis of the combined 3D image data record obtained from the 2D image data 5. For this reverse transformation of the vascular section into the original 3D form the transformation parameters stored in the transformation step are read out and applied in inverse manner. In the present example, in this step all merged data, i.e. both the 2D image data 5 and the 3D image data record 11 formed therefrom as well as the anatomical transformed 3D image data 9 are reverse transformed. The result is the registration of the anatomical 3D image data 8 with the sequence of 2D image data 5 of the imaging instrument. This 2D image data 5 of the vascular section under examination now exists registered and can additionally be arranged or reconstructed in accordance with the true 3D anatomy.

The invention claimed is:

1. A method of registering a sequence of two-dimensional image data with three-dimensional image data of a hollow canal, the two-dimensional image data recorded by a medical endoluminal imaging device, wherein a current relative displacement of the imaging device in the hollow canal is detected and recorded during the recording of each individual two-dimensional image data set of the sequence, the method comprising:

determining a three-dimensional progression of a longitudinal axis of at least a section of the hollow canal using the three-dimensional image data;

transforming the three-dimensional progression into a rectilinear progression by transforming the three-dimensional image data related to the section of the hollow canal;

determining and recording a set of transformation parameters describing the transformation of the three-dimensional data related to the section of the hollow canal;

generating a combined three-dimensional image data record by stringing together the sequence of two-dimension image data relative to a central straight line, the individual two-dimensional image data sets included in the sequence of two-dimensional image data spaced apart according to the current relative displacement;

registering the combined three-dimensional image data record with the transformed three-dimensional image data related to the section of the hollow canal by equating the central straight line with the rectilinear progression and displacing the combined three-dimensional image data record so that a reference location present in both the combined three-dimensional image data record and the transformed three-dimensional data related to the section of the hollow canal overlaps after the translation; and registering the displaced combined three-dimensional image data record or two-dimensional image data included in the displaced combined three-dimensional image data record with the three-dimensional image data using the recorded set of transformation parameters, wherein the displaced combined three-dimensional image data record or the two-dimensional image data included in the displaced combined three-dimensional image data record is further transformed using a transformation algorithm representing a reverse transformation relative to the transformation described by the set of transformation parameters.

2. The method according to claim 1, wherein image resolutions of the three-dimensional image data and the combined three-dimensional image data record are matched using an interpolation algorithm.

3. The method according to claim 1, wherein the reference location is a visually striking location point present in both the combined three-dimensional image data record and the transformed three-dimensional data related to the section of the hollow canal.

4. The method according to claim 1, wherein the three-dimensional progression includes segmenting the three-dimensional image data of a wall of the hollow canal.

5. The method according claim 1, wherein the three-dimensional image data of the hollow canal are recorded by a magnetic resonance device or an X-ray device.

6. The method according to claim 1, wherein the two-dimensional image data are recorded by an IVUS catheter.

7. The method according to claim 1, wherein the two-dimensional image data are recorded by an OCT catheter.

8. The method according to claim 1, wherein the two-dimensional image data are recorded by a fluorescent imaging device.

9. The method according to claim 1, wherein the hollow canal is a vessel.

* * * * *